United States Patent
Loreth

(10) Patent No.: US 9,622,756 B2
(45) Date of Patent: Apr. 18, 2017

(54) ARTHROSCOPIC RESECTION METHODS

(71) Applicant: Brian J. Loreth, Braintree, MA (US)

(72) Inventor: Brian J. Loreth, Braintree, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/860,464

(22) Filed: Apr. 10, 2013

(65) Prior Publication Data

US 2013/0231670 A1 Sep. 5, 2013

Related U.S. Application Data

(62) Division of application No. 13/070,584, filed on Mar. 24, 2011, now abandoned.

(60) Provisional application No. 61/316,860, filed on Mar. 24, 2010, provisional application No. 61/443,301, filed on Feb. 16, 2011.

(51) Int. Cl.
*A61B 17/16* (2006.01)
*A61B 17/32* (2006.01)

(52) U.S. Cl.
CPC .......... *A61B 17/16* (2013.01); *A61B 17/1615* (2013.01); *A61B 17/1631* (2013.01); *A61B 17/1633* (2013.01); *A61B 17/32002* (2013.01); *A61B 17/1628* (2013.01); *A61B 17/1662* (2013.01); *A61B 2017/1602* (2013.01)

(58) Field of Classification Search
CPC . A61B 17/16; A61B 17/1615; A61B 17/1659; A61B 17/32003; A61B 17/3207; A61B 17/320758; A61B 17/320775; A61B 2017/1602; A61B 17/1604; A61B 17/1637

USPC ........ 606/79-85, 167, 169-171, 180; 604/22
See application file for complete search history.

(56) References Cited

U.S. PATENT DOCUMENTS

| | | | |
|---|---|---|---|
| 5,047,040 A * | 9/1991 | Simpson et al. | 606/159 |
| 5,759,185 A * | 6/1998 | Grinberg | 606/80 |
| 5,913,867 A | 6/1999 | Dion | |
| 6,045,305 A * | 4/2000 | Plummer | 408/230 |
| 6,258,093 B1 | 7/2001 | Edwards et al. | |
| 6,419,684 B1 | 7/2002 | Heisler et al. | |
| 7,207,752 B2 * | 4/2007 | Schulte | 408/224 |
| 2002/0090273 A1 * | 7/2002 | Serwa | 409/132 |

(Continued)

FOREIGN PATENT DOCUMENTS

| | | |
|---|---|---|
| DE | 8418723 U | 9/1984 |
| DE | 19639193 A1 | 4/1998 |

(Continued)

OTHER PUBLICATIONS

International Search Report, PCT/US2011/029708, dated Aug. 29, 2011, pp. 5.

(Continued)

*Primary Examiner* — Kathleen Holwerda

(57) ABSTRACT

The present disclosure relates to resection devices and methods. The resection device includes an outer tubular member; and an inner tubular member disposed within the outer tubular member, the inner tubular member including a burr having a body with flutes extending along a length of the body, the flutes including parabolic wave patterns located along surface edges of the flutes. In an embodiment, the parabolic wave patterns extend along entire lengths of the flutes. Other resection devices and methods are also disclosed.

29 Claims, 3 Drawing Sheets

(56) References Cited

U.S. PATENT DOCUMENTS

| | | |
|---|---|---|
| 2005/0283160 A1 | 12/2005 | Knisely et al. |
| 2008/0132929 A1* | 6/2008 | O'Sullivan et al. .......... 606/170 |
| 2008/0140078 A1* | 6/2008 | Nelson et al. .................. 606/80 |
| 2009/0048602 A1 | 2/2009 | O'Donoghue |
| 2010/0312338 A1 | 12/2010 | Gonzales et al. |
| 2011/0015667 A1 | 1/2011 | Gonzales et al. |
| 2011/0015734 A1 | 1/2011 | Gonzales et al. |
| 2011/0022172 A1 | 1/2011 | Gonzales et al. |

FOREIGN PATENT DOCUMENTS

| | | |
|---|---|---|
| WO | 9827876 A1 | 7/1998 |
| WO | 2007142830 A2 | 12/2007 |
| WO | 2008145380 A1 | 12/2008 |
| WO | 2010141850 | 12/2010 |

OTHER PUBLICATIONS

EPO Second Office Action, Appln. No. 11714167.1-1654, Applicant Smith & Nephew, dated Jan. 21, 2015.
Australian Patent Examination Report No. 1 dated Apr. 7, 2015 for Australian Patent Application No. 2011232446.
Notice of Reasons for Rejection, Japanese Application No. 2013-501441, Mailed May 25, 2015.
Second Office Action State Intellectual Property Office, P.R. China for Chinese Appln No. 201180015765, Oct. 14, 2015.
Australian Patent Examination Report No. 2, Patent Application N. 2011232446, Dated Dec. 4, 2015.
Office Action for Canadian Patent Application No. 2,759,817 mailed on Jan. 20, 2016.

* cited by examiner

ARTHROSCOPIC RESECTION METHODS

CROSS REFERENCE TO RELATED APPLICATIONS

This application is a divisional of U.S. patent application Ser. No. 13/070,584 filed Mar. 24, 2011 entitled ARTHROSCOPIC RESECTION DEVICES, which claims benefit of the priority of U.S. Provisional Patent Application No. 61/316,860 filed Mar. 24, 2010 and U.S. Provisional Patent Application No. 61/443,301 filed Feb. 16, 2011.

TECHNICAL FIELD

The present disclosure relates to arthroscopic resection devices and methods for resection of tissue.

BACKGROUND

Arthroscopic resection devices have been used in performing closed surgery, such as endoscopic surgery, i.e. arthroscopic surgery. Generally, these devices include, without limitation, blade devices and burr devices. Both the blade and burr devices include an elongate outer tubular member terminating at a distal end having an opening in the side wall and/or the end wall to form a cutting port or window. Both devices also include an elongate inner tubular member coaxially disposed in the outer tubular member and having a distal end disposed adjacent the port/window in the distal end of the outer tubular member. The distal end of the inner tubular member of the blade device has a surface or edge for engaging tissue via the port/window in the distal end of the outer tubular member and in many cases cooperates with the port/window to shear or cut tissue. Alternatively, the distal end of the inner tubular member of the of the burr device has a burr having helical grooved surfaces or flutes for drilling and grinding tissue via the port/window in the distal end of the outer tubular member and in many cases cooperates with the port/window to shear or cut tissue. The inner tubular members are rotatably driven at their proximal ends, normally via a hand piece having a small electric motor therein controlled by finger-actuated switches on the hand piece. A foot switch or switches on a console supply power to the hand piece.

The helical flutes of the burr tend to not have any additional distinguishing geometrical features designed to enhance performance. They typically have smooth, non-serrated cutting edges and follow the design of end mills or drills. Additionally, the burrs tend to have the same number of flutes along the entire body of the burr. The surfaces or edges of the blade device inner member typically have straight cutting edges.

The characteristics of these cutting features result in a less aggressive cutting action, thereby resecting the tissue or bone into larger fragments that increase the chances of the device becoming clogged, as well as cloud the image a surgeon has inside the surgical area. Additionally, these characteristics increase the possibility of the device displaying unpleasant harmonics or resonance during use. Furthermore, having the same number of flutes along the body of the burr allows for only one style of cutting, thereby providing the burr device with less versatility. Therefore, arthroscopic resection devices that alleviate these limitations are needed.

SUMMARY

In an aspect, the present disclosure relates to a resection device. The resection device includes an outer tubular member; and an inner tubular member disposed within the outer tubular member, the inner tubular member including a burr having a body with flutes extending along a length of the body, the flutes including parabolic wave patterns located along surface edges of the flutes. In an embodiment, the parabolic wave patterns extend along entire lengths of the flutes.

In another aspect, the present disclosure relates to a resection device. The resection device includes an outer tubular member; and an inner tubular member disposed within the outer tubular member, the inner tubular member including a burr having a body with flutes extending along a length of the body and a tip with flutes, wherein the tip and the body include a different number of flutes. In an embodiment, the body has a higher number of flutes than the tip. In another embodiment, the body has a lower number of flutes than the tip.

In yet another embodiment, the flutes on either the body or the tip include parabolic wave patterns located along surface edges of the flutes. In a further embodiment, the device further includes a transition piece located between the inner tubular member and the burr, the transition piece including a proximal portion and a tapered distal portion. In yet a further embodiment, the device further includes an opening located between the inner tubular member and the burr. In an embodiment, the opening leads to a passageway, the passageway extending along a length of the inner tubular member.

In yet another aspect, the present disclosure relates to a resection device. The resection device includes an outer tubular member; and an inner tubular member disposed within the outer tubular member, the inner tubular member including a burr having a body with flutes extending along a length of the body and a tip with flutes, wherein the tip and the body include a different number of flutes, the flutes on either the body or the tip including parabolic wave patterns located along surface edges of the flutes.

In still another aspect, a surgical method is disclosed that includes providing an arthroscopic resection device including an outer tubular member, and an inner tubular member disposed within the outer tubular member. The inner tubular member includes an arthroscopic burr having a body with flutes extending along a length of the body and a tip with flutes, such that the tip and the body include a different number of flutes. The surgical method further includes performing an arthroscopic resection procedure on target tissue using the arthroscopic resection device.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

The disclosures of U.S. patent application Ser. No. 13/070,584 filed Mar. 24, 2011, U.S. Provisional Patent Application No. 61/316,860 filed Mar. 24, 2010, and U.S. Provisional Patent Application No. 61/443,301 filed Feb. 16, 2011, are hereby incorporated herein by reference in their entirety.

The following description of the preferred embodiment(s) is merely exemplary in nature and is in no way intended to limit the disclosure, its application, or uses.

Figure 1:
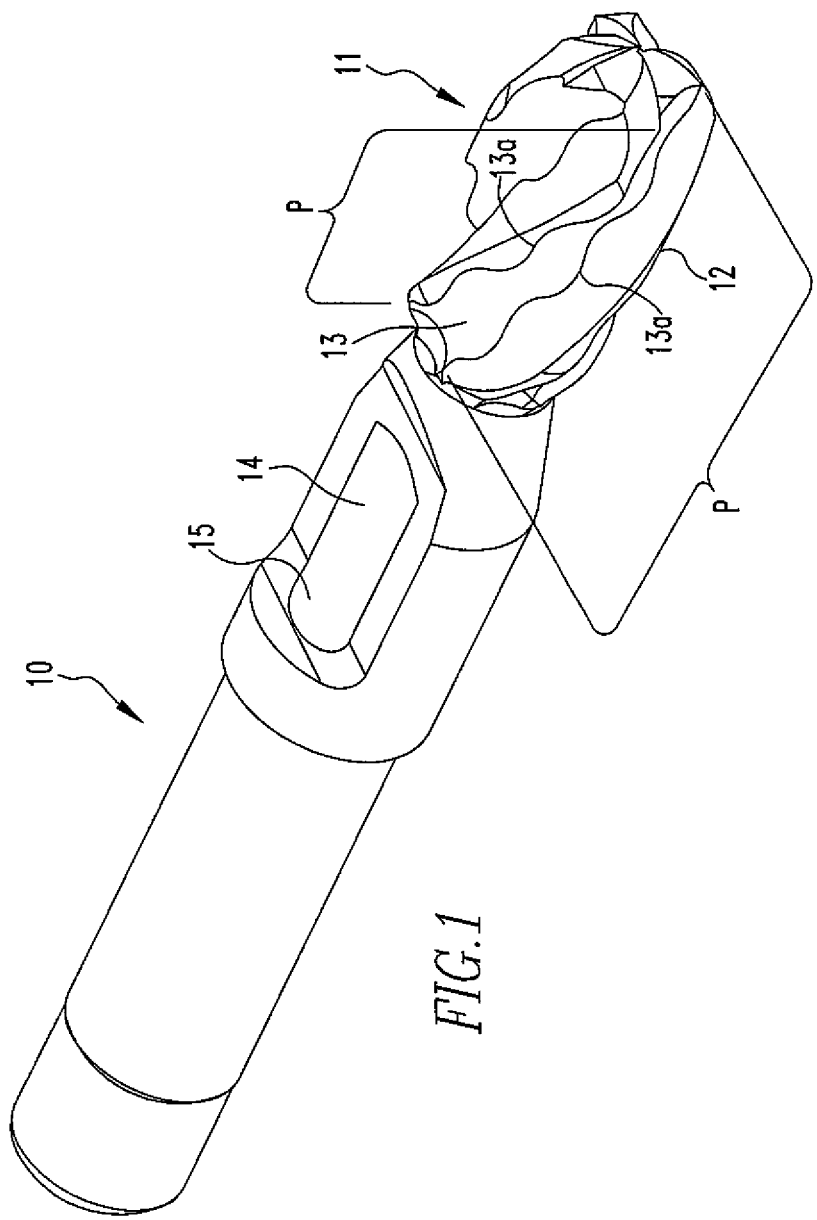
FIG. 1 shows a first embodiment of an inner tubular member of the present disclosure.
Figure 2:
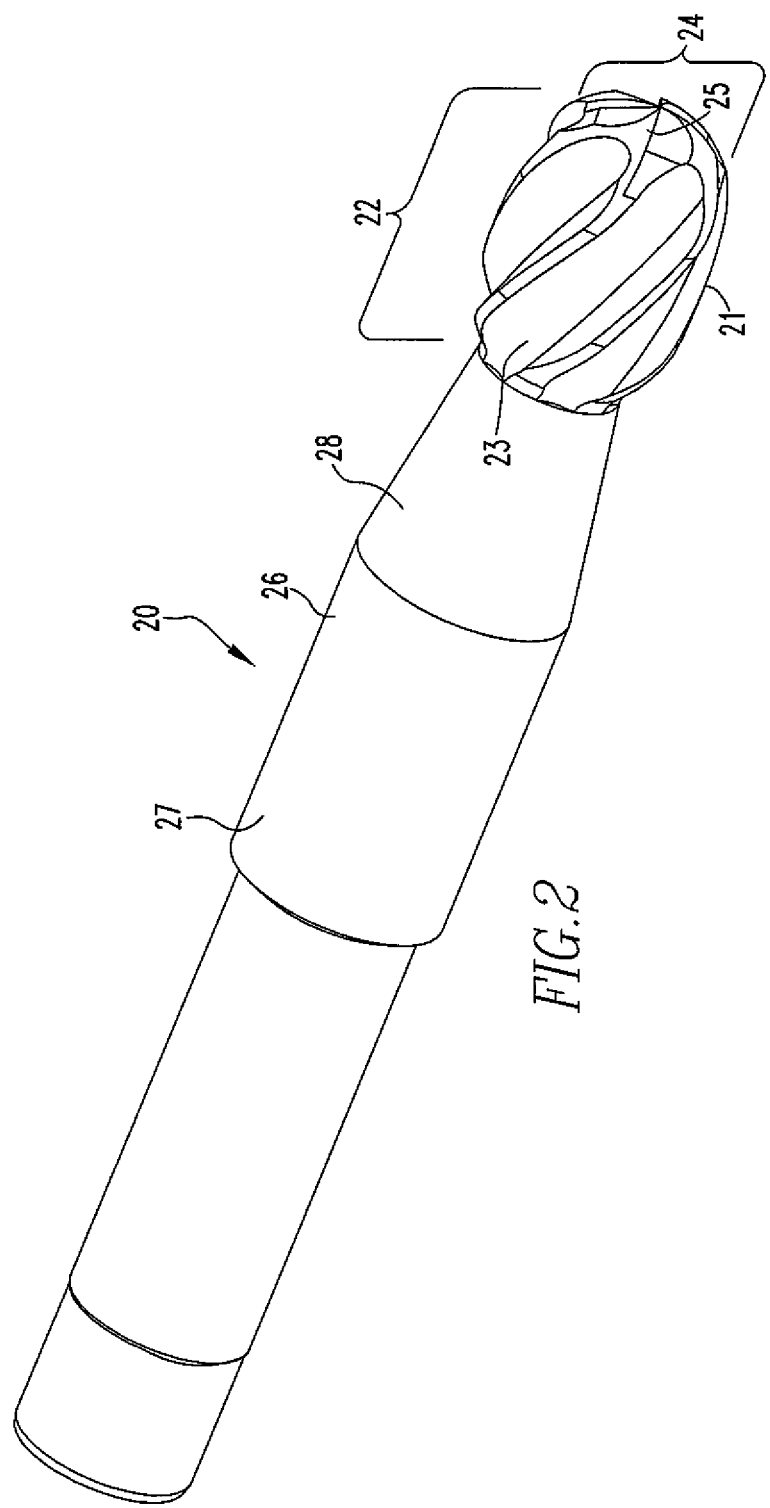
FIG. 2 shows a second embodiment of an inner tubular member of the present disclosure.
Figure 3:
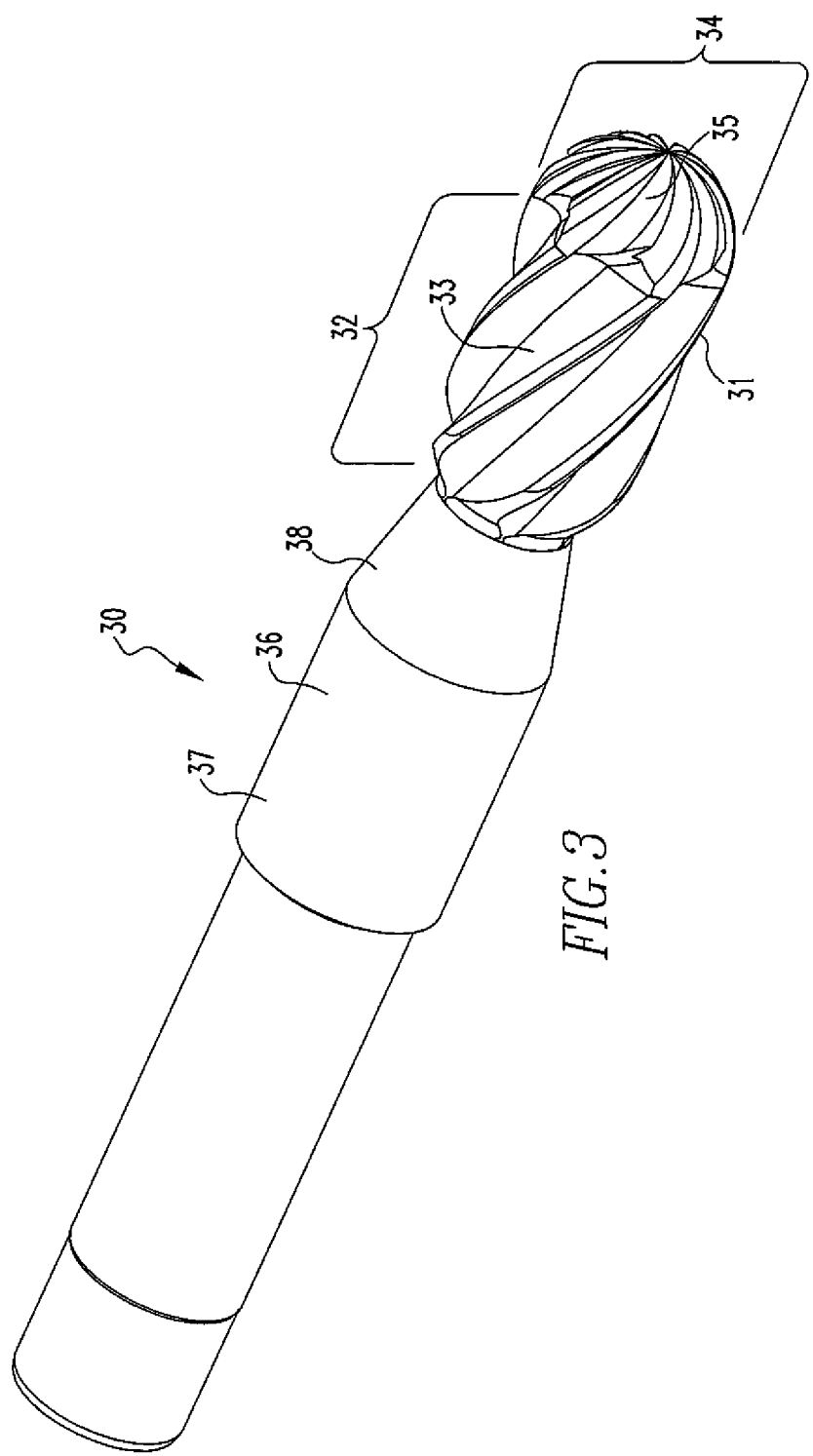
FIG. 3 shows a third embodiment of an inner tubular member of the present disclosure.

FIGS. 1-3 show inner tubular members for use with burr devices and, specifically, the distal ends of the members. FIG. 1 shows an inner tubular member 10 including a burr 11 having a body 12 with helical flutes 13 extending along the length of the body 12. The surface edges 13a of the flutes 13 incorporate parabolic wave patterns P along the entire lengths of the flutes 13. The burr 11 may have any number of flutes 13 and the flutes 13 may be located at any angle relative to a longitudinal axis passing through the burr 11. Additionally, the flutes 13 may incorporate a pattern having an alternate geometry that may not be truly parabolic, but has the cutting characteristics of the parabolic wave pattern.

Located proximal to the burr 11 and between the inner tubular member 10 and the burr 11 is an opening 14 to a passageway 15 extending the length of the inner tubular member 10. The passageway 15 allows for the flow of fragmented tissue and bone during surgery. A vacuum (not shown) is attached to a proximal end (not shown) of the member 10 for vacuuming the tissue through the passageway 15.

The parabolic wave patterns P on the flutes 13 provide the burr 11 with a more aggressive cutting action, especially when used in cutting bone, which causes the burr 11 to cut the bone into smaller fragments. Having smaller bone fragments allows the fragments to be removed more readily by the vacuum, thereby reducing the possibility of clogging and obscuring the visual image of the surgical area. Additionally, the parabolic wave pattern P deliberately creates inconsistencies in the burr geometry, thereby lessening any unpleasant harmonics or resonance of the burr device. This lessening, coupled with the fact the pattern P yields constant acceleration, provides the device with smoother cutting performance and controllability.

FIG. 2 shows another inner tubular member 20 including a burr 21 having a body 22 with helical flutes 23 extending along the length of the body 22 and a tip 24 also having helical flutes 25. The tip 24 has a lower number of flutes 25 than the body 22. Having a lower number of flutes 25 on the tip 24 makes the tip 24 cut more aggressively than the body 22 because the individual cutting area of each flute 25 is more. FIG. 3 shows yet another inner tubular member 30 including a burr 31 having a body 32 with helical flutes 33 extending along the length of the body 32 and a tip 34 with helical flutes 35. Unlike member 20, the tip 34 of burr 31 has a higher number of flutes 35 than the body 32. Having a higher number of flutes 35 on the tip 34 makes the tip 34 cut less aggressively than the body 32 because the individual cutting area of each flute 35 is less.

Having a transitional fluted burr with a different number of flutes on the tip than on the body provides more versatility to the user. The ability to perform different cutting techniques with one burr is more efficient than using two different devices. Additionally, it is more cost effective to use this type of burr due to only one burr having to be inventoried and utilized.

Any different number combination of flutes may be used on the burrs 21,31 and the flutes 23,25,33,35 may be located at any angle relative to a longitudinal axis passing through the burr 21,31. Additionally, it is within the scope of this disclosure to have parabolic wave patterns along the lengths of any of the flutes 23,25,33,35, similar to the wave patterns P on flutes 13. The patterns may be located on the surface edges of the flutes 23,25,33,35 and along the entire length or along a partial length of the flutes 23,25,33,35. Furthermore, it is within the scope of this disclosure to have an alternating number of flutes having the wave patterns. Even further, the flutes 23,25,33,35 may incorporate a pattern having an alternate geometry that may not be truly parabolic, but has the cutting characteristics of the parabolic wave pattern.

Both burrs 21,31 are coupled to transition pieces 26,36 located between the inner tubular members 20,30 and the burrs 21,31. The transition pieces 26,36 include proximal portions 27,37 and tapered distal portions 28,38. In use, all of the members 10,20,30 would be disposed within an outer tubular member, as discussed above.

The inner tubular members 10,20,30 and their components are made from metal material. However, other material strong enough to withstand the forces of a tissue cutting action may be used. The flutes, parabolic wave patterns on the flutes, and opening are made via a machining process or other process known to those of skill in the art.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical method, comprising:
   locating an arthroscopic resection device so that a distal end thereof is proximal target tissue;
   wherein the arthroscopic resection device includes:
     an outer tubular member, and an inner tubular member rotatably disposed within the outer tubular member, the inner tubular member having an arthroscopic burr including a body and a tip,
     wherein the body comprises flutes and the tip comprises flutes, wherein each of the flutes on the body extend along a length of the body, and the flutes on the body are arranged so an alternating number of the flutes on the body include parabolic wave patterns located along surface edges of the flutes on the body,
     wherein a respective parabolic wave pattern is arranged along a surface edge of a respective flute on the body so as to form a cutting edge portion with an undulating parabolic wave pattern; and
   performing an arthroscopic resection procedure on the target tissue using the arthroscopic resection device, wherein said performing further includes manipulating the arthroscopic resection device and rotating the inner tubular member including the arthroscopic burr so that the surface edge of the respective flute on the body with the parabolic wave pattern rotatably contacts the target tissue during processing of the target tissue.

2. The method of claim 1, wherein the inner tubular member including the arthroscopic burr is configured such that a quantity of the flutes on the body is higher than a quantity of the flutes on the tip.

3. The method of claim 1 wherein the inner tubular member including the arthroscopic burr is configured such that a quantity of the flutes on the body is lower than a quantity of the flutes on the tip.

4. The method of claim 1, wherein the inner tubular member is arranged such that either the body or the tip includes at least one flute without parabolic wave patterns located along surface edges of the at least one flute.

5. The method of claim 1, wherein the inner tubular member is further configured so as to include a through aperture that is located between a proximal end of the inner tubular member and the arthoscopic burr, the through aperture being configured to receive effluent from operation of the arthroscopic burr and wherein said method further includes removing the effluent being produced via the through aperture.

6. The method of claim 1, wherein each flute on the body of the arthroscopic resection device is arranged to include parabolic wave patterns located along the surface edges of the flutes on the body.

7. The method of claim 1, wherein the alternating number of the flutes on the body including parabolic wave patterns further comprises flutes on the body comprising opposing surface edges that each extend along the length of the body and so that each such surface edge is configured to include parabolic wave patterns.

8. The method of claim 1, wherein the alternating number of the flutes on the body including parabolic wave patterns further comprises a leading surface edge and a trailing surface edge and wherein the leading and trailing surface edges are each arranged so each presents parabolic wave patterns.

9. The surgical method of claim 1, wherein the surface edge of the respective flute on the body is further arranged so that the undulating parabolic wave pattern includes a successive pattern of a peak and a valley.

10. The surgical method of claim 9, wherein the surface edge of the respective flute on the body is further arranged so that the successive pattern of the peak and valley is arranged so as to extend downwardly into a channel defined by the respective flute on the body.

11. The method of claim 10, wherein the alternating number of the flutes on the body including parabolic wave patterns further comprises a leading surface edge and a trailing surface edge and wherein the leading and trailing surface edges are each configured with parabolic wave patterns.

12. The surgical method of claim 1, wherein the surface edge of the respective flute on the body is further arranged so that the undulating parabolic wave pattern extends downwardly into a channel defined by the respective flute on the body.

13. A surgical method comprising:
locating an arthroscopic resection device so that a distal end thereof is proximal to target tissue;
wherein the arthroscopic resection device includes:
an outer tubular member and an inner tubular member disposed within the outer tubular member, the inner tubular member including an arthroscopic burr having a body with flutes extending along a length of the body and a tip with flutes,
wherein the tip and the body include a different number of flutes,
wherein an alternating number of the flutes on at least the body of the arthroscopic burr include parabolic wave patterns located along surface edges of the alternating number of the flutes on at least the body,
wherein the parabolic wave patterns of a respective flute are arranged along a surface edge of the respective flute so the surface edge forms a cutting edge portion with an undulating parabolic wave pattern, the cutting edge portion being in circumferential direction with respect to a longitudinal direction of the inner tubular member; and
performing an arthroscopic resection procedure on target tissue using the arthroscopic resection device, wherein said performing further includes manipulating the arthroscopic resection device and rotating the inner tubular member including the arthroscopic burr with respect to the outer tubular member so that at least one of the body or tip of the burr is in contact with the target tissue and so at the surface edges of the flutes with the parabolic wave patterns rotatably contact the target tissue during processing of the target tissue.

14. The method of claim 13, wherein the inner tubular member including the arthroscopic burr is configured and arranged with the body having a higher number of flutes than the tip.

15. The method of claim 13, wherein the inner tubular member including the arthroscopic burr is configured and arranged with the body having a lower number of flutes than the tip.

16. The method of claim 13, wherein the inner tubular member is arranged such that either the body or the tip includes, between the alternating number of the flutes on at least the body, at least one flute without parabolic wave patterns located along surface edges of the at least one flute.

17. The method of claim 13, wherein the inner tubular member is further configured so as to include an aperture that is located between a proximal end of the inner tubular member and the arthroscopic burr, the aperture being configured to receive effluent from operation of the arthroscopic burr and wherein said method further comprises removing the effluent being produced via the through aperture.

18. The method of claim 13, wherein each flute on the body is arranged to include parabolic wave patterns located along the surface edges of the flutes on the body.

19. The method of claim 13, wherein the alternating number of the flutes on at least the body including parabolic wave patterns further comprise opposing surface edges that each extend along the length of the body and so that each such surface edge is configured so as to include the parabolic wave patterns.

20. The surgical method of claim 13, wherein the surface edge of the respective flute is further arranged so that the undulating parabolic wave pattern includes a successive pattern of a peak and a valley.

21. The surgical method of claim 20, wherein the surface edge of the respective flute is further arranged so that the successive pattern of the peak and valley is arranged so as to extend downwardly into a channel defined by the respective flute.

22. The surgical method of claim 13, wherein the surface edge of the respective flute is further arranged so that the undulating parabolic wave patterns extends downwardly into a channel defined by the flute.

23. A surgical method, comprising the steps of:
locating an arthroscopic resection device within a body, the arthroscopic resection device including an outer tubular member, an inner tubular member, and an arthroscopic burr, wherein said locating further includes locating the arthroscopic burr proximal to target tissue within the body;

wherein the arthroscopic resection device is arranged such that:

(a) the inner tubular member is rotatably disposed within the outer tubular member, (b) a distal end of the inner tubular member is secured to the arthroscopic burr, (c) the arthroscopic burr includes a body portion and a tip portion, where the body and tip portions are each configured so as to include flutes each having a cutting edge, (d) an alternating number of the flutes on at least the body portion are configured so surface edges of the alternating number of the flutes each include parabolic wave patterns, (e) the parabolic wave patterns are further arranged along the surface edges to form a cutting edge portion with an undulating parabolic wave pattern, the cutting edge portion being in a circumferential direction with respect to a longitudinal direction of the inner tubular member, and (f) the arthroscopic burr is further configured so that one of the tip portion or the body portion has a lower number of flutes with cutting edges than the other of the body portion or the tip portion: and performing an arthroscopic resection procedure on the target tissue using the arthroscopic resection device, wherein said performing further includes manipulating the arthroscopic resection device and rotating the inner tubular member and the arthroscopic burr with respect to the outer tubular member so that at least one of the body portion or tip portion of the burr is in contact with the target tissue and so at least the surface edges with the parabolic wave patterns rotatably contact the target tissue during processing of the target tissue.

24. The method of claim 23, wherein:

the inner tubular member of the provided arthroscopic resection device is further configured so as to include a through aperture that is located between a proximal end of the inner tubular member and the arthroscopic burr; and said performinq further includes removing effluent from the body via the through aperture during rotating of the arthroscopic burr during the arthroscopic resection procedure.

25. The method of claim 23, wherein the surface edges of each flute of the alternating number of the flutes on at least the body portion include opposing surface edges that each extend along the length of a respective flute, wherein each opposing surface edge is arranged to include parabolic wave patterns.

26. The method of claim 23, wherein the surface edges of each flute of the alternating number of the flutes on at least the body portion include a leading surface edge and a trailing surface edge and wherein the leading and trailing surface edges are each arranged so each presents parabolic wave patterns.

27. The surgical method of claim 23, wherein the undulating parabolic wave pattern includes a successive pattern of a peak and a valley.

28. The surgical method of claim 27, wherein the successive pattern of the peak and valley is arranged so as to extend downwardly into a channel defined by a respective flute of the alternating number of the flutes on at least the body portion.

29. The surgical method of claim 23, wherein the undulating parabolic wave pattern is arranged to extend downwardly into a channel defined by a respective flute of the alternating number of the flutes on at least the body portion.

* * * * *